United States Patent [19]

Levine

[11] Patent Number: 5,195,515

[45] Date of Patent: Mar. 23, 1993

[54] HEATED CARTRIDGE HUMIDIFIER AND HUMIDIFICATION CHAMBER FOR USE THEREWITH

[76] Inventor: Walter Levine, 6948 N. Keating, Lincolnwood, Ill. 60646

[21] Appl. No.: 861,315

[22] Filed: Mar. 31, 1992

Related U.S. Application Data

[63] Continuation-in-part of Ser. No. 665,402, Mar. 6, 1991, abandoned.

[51] Int. Cl.[5] .............................................. A61M 16/00
[52] U.S. Cl. ............................ 128/203.26; 128/203.16; 128/203.17; 128/204.17
[58] Field of Search ....................... 128/203.12, 203.16, 128/203.17, 204.14, 204.17, 203.26

[56] References Cited

U.S. PATENT DOCUMENTS

| | | | |
|---|---|---|---|
| 4,051,205 | 9/1977 | Grant | 261/70 |
| 4,110,419 | 8/1978 | Miller | 261/142 |
| 4,225,542 | 9/1980 | Wall et al. | 128/203.26 |
| 4,366,105 | 12/1982 | Nowacki | 261/35 |
| 4,500,480 | 2/1985 | Cambio, Jr. | 261/104 |
| 4,674,494 | 6/1987 | Wiencek | 128/203.16 |
| 4,765,327 | 8/1988 | Shim | 128/204.13 |
| 4,913,140 | 4/1990 | Orec et al. | 128/203.26 |
| 4,926,856 | 5/1990 | Cambio, Jr. et al. | 128/203.26 |

OTHER PUBLICATIONS

Operator's manual, The bird® Humidifier, ©Bird Corporation/3M, 1979, Form L867R2, 25 pages total.

Primary Examiner—Edgar S. Burr
Assistant Examiner—Aaron J. Lewis
Attorney, Agent, or Firm—Welsh & Katz, Ltd.

[57] ABSTRACT

A disposable heated cartridge humidifier for use with a collapsible water supply container and a heating device, the humidifier adapted for heating and humidifying a breathable gas to be inhaled by a patient. The humidifier includes a humidifier housing having an open upper end. A cap portion sealingly engages the open upper end of the humidifier housing to define a humidifier chamber, and has a gas inlet port, a gas delivery port, and a water delivery port adapted to receive water from the container, all of the ports being in fluid communication with the humidifier housing. The present heated cartridge humidifier also includes a water feed tube depending from an underside of the cap portion, and a float retaining tube circumscribes the feed tube, depends from the underside of the cap portion, is in fluid communication with the humidifier housing and retains a float therein. The float is slidingly retained in the float retaining tube for sealingly engaging a lower end of the water feed tube when the water level in the housing reaches a specified level.

31 Claims, 4 Drawing Sheets

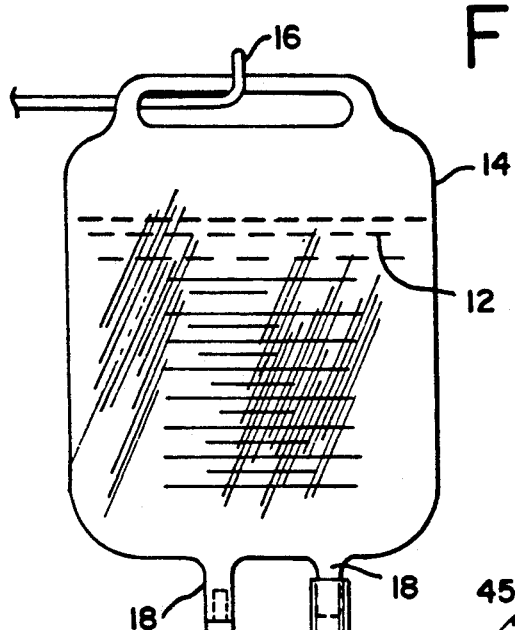
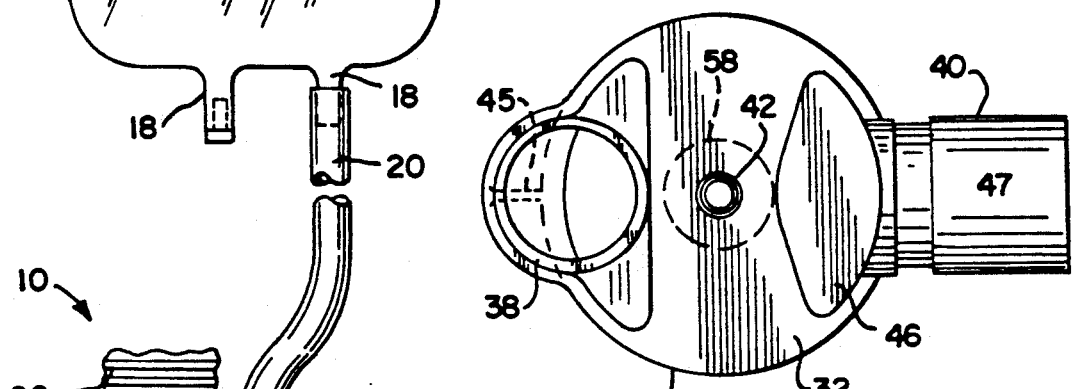
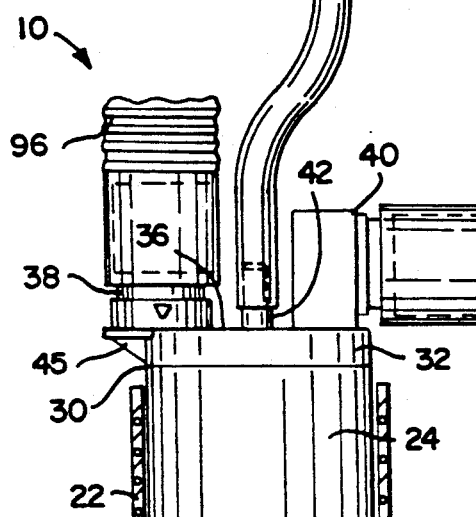
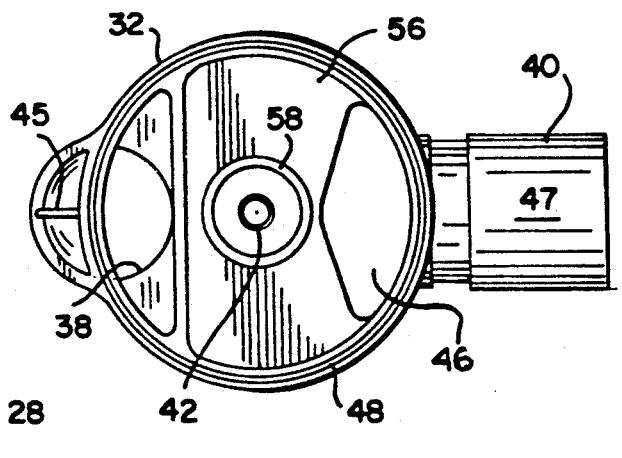
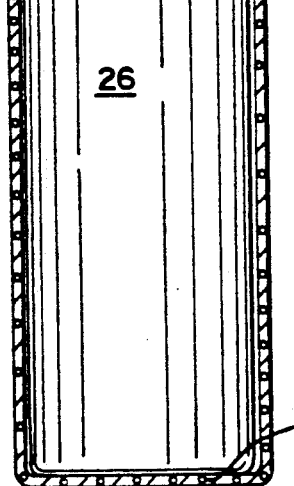

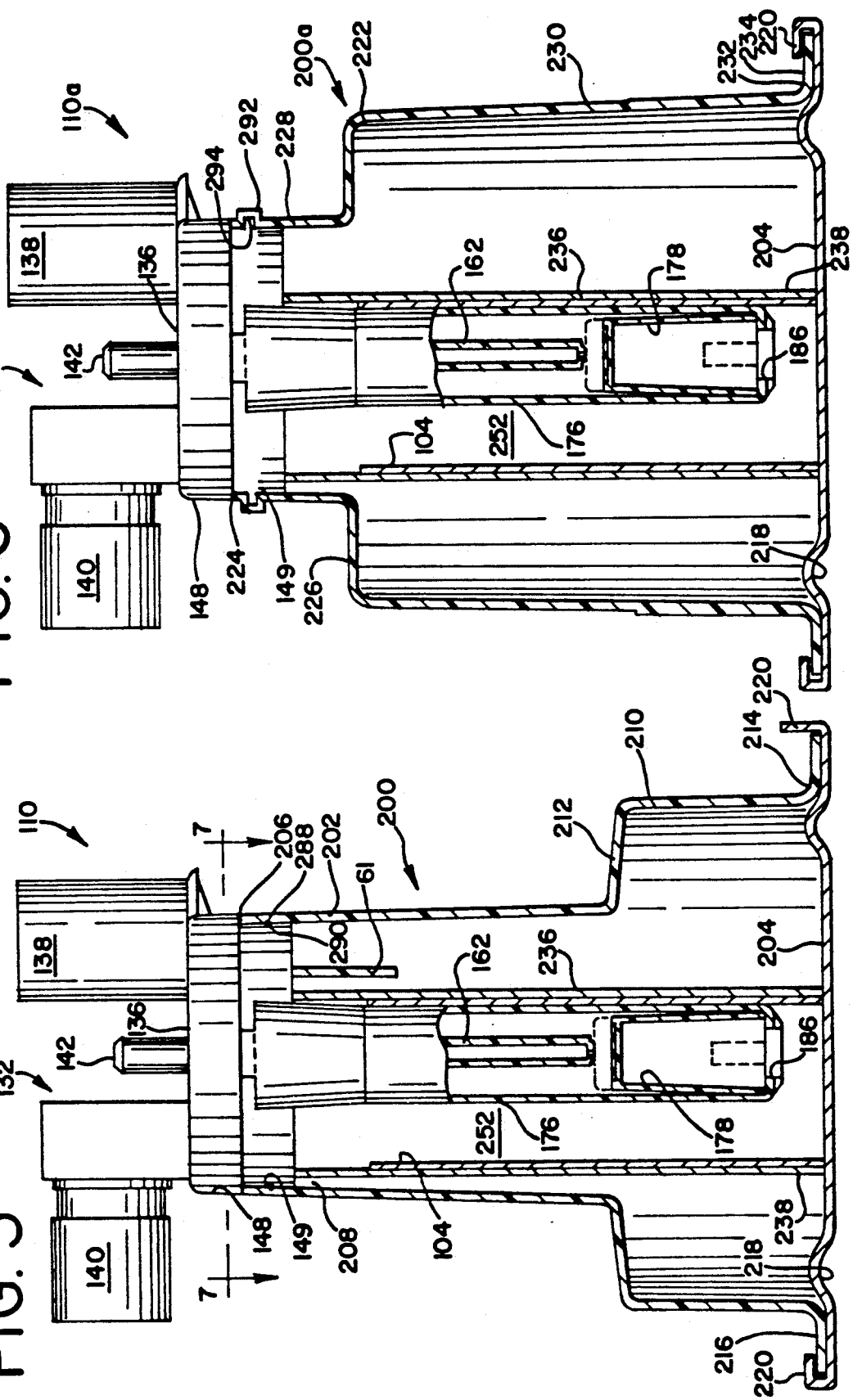

HEATED CARTRIDGE HUMIDIFIER AND HUMIDIFICATION CHAMBER FOR USE THEREWITH

RELATED APPLICATION

This application is a continuation-in-part of Ser. No. 07/665,402, filed Mar. 6, 1991 now abandoned, and entitled: HEATED CARTRIDGE HUMIDIFIER.

BACKGROUND OF THE INVENTION

The present invention relates generally to devices for delivering gases having a controlled vapor level and temperature to a delivery point, and more particularly to humidifier devices employing disposable humidifier cartridges which receive water from an adjacent container.

When a normally healthy person breathes atmospheric air, his air passages supply heat and moisture to the inhaled gases, with the body being able to supply the required amount of heat and moisture. However, when subject to certain medical conditions, a patient's mechanism of supplying heat and moisture is disrupted, and it becomes necessary to provide an artificial system for warming inspired gases to a point at or near normal body temperature before the gas is delivered to the patient. Accordingly, it is necessary to humidify the inspired gases to a level at or near full (100%) moisture saturation.

Conventional systems for providing heated and moisturized respiratory gases basically fall into two groups: nebulizers, which produce aerosols of fine water droplets, and heated humidifiers, which supply heat and moisture to a gas by the passage of the gas through or over a heated water bath or evaporative surface. The present invention is concerned with the latter group of devices.

One such humidifier system includes a rigid, refillable water container designed to be placed upon a base unit having a heating element. The container is divided into an upper reservoir section, and a lower humidifier chamber by a partition having a small diameter vertical port therein. Water flows by gravity from the reservoir section through the port into the humidifier chamber, through which a stream of gas flows to be heated and humidified.

A float valve controls the water level in the humidifier by sealing the port when the maximum specified water level is attained. As water is used, the water level in the humidifier chamber falls, opening the port to allow additional water to enter from the reservoir section. A major disadvantage of this type of humidifier is that the reservoir must be refilled from another container, a process which requires that the reservoir be opened, subjecting it to bacterial contamination. Another disadvantage of the rigid, capped reservoir section is that the reservoir is not vented, which may interfere with the free flow of water due to the creation of a vacuum in the reservoir.

Another conventional system employs a vertically oriented, cylindrical humidifier chamber which is fed water through a port in the lower end. A tube connects the lower end of the humidifier chamber to the lower end of a rigid, disposable water container. An upper portion of the humidifier chamber includes gas inlet and delivery ports, as well as a vent port connecting the chamber with an upper end of the water supply container. A float valve in the humidifier chamber blocks the flow of air into the vent line as the water level rises in the chamber, thus preventing the entry of water into the humidifier chamber from the supply container.

By venting the supply container, the problem of irregular water flow identified in the previous example is eliminated. However, a potentially more serious problem is created, i.e., the possibility of airborne bacteria exhaled by the patient entering the humidifier chamber and contaminating the supply water through the vent tube.

There are several types of heated humidifier units presently available to hospitals, and many of these have the inherent problems of susceptibility to contamination, and relatively excessive operator maintenance. Of these available units, many are designed for use with relatively expensive heater base units which are an obstacle to conversion to more efficient and less contamination-prone disposable devices.

Thus, there is a need for a disposable humidifier system which does not mix the patient's exhalate with the supply water, which prevents bacterial contamination of the supply water by other means, and which is adaptable to at least one and preferably more of the variety of evaporative heater base units currently in use by hospitals and respiratory practitioners. There is also a need for a cartridge humidifier system which is simple in its operation, and is inexpensive to manufacture and assemble.

SUMMARY OF THE INVENTION

Accordingly, the present invention addresses the above-identified drawbacks of conventional devices by providing a heated cartridge humidifier designed for use with collapsible, gravity-feed, sterile water supply bags. The present cartridge includes a simple float valve apparatus in which the flow of incoming water into the humidifier chamber is directly regulated.

More specifically, the present invention provides a disposable heated cartridge humidifier for use with a collapsible, gravity feed water supply container and an external heating device, the humidifier adapted for heating and humidifying a breathable gas to be inhaled by a patient undergoing respiratory therapy and/or anesthesia. The humidifier includes a housing configured to be heated by the heating device, and also has an open upper end. A cap portion sealingly engages the open upper end of the housing and has a gas inlet port, a gas delivery port, and a and a water delivery port adapted to receive water from the container, all of the ports being in fluid communication with the housing.

The present heated cartridge humidifier also includes a water feed tube depending from an underside of the cap portion. A float retaining tube circumscribes the feed tube, depends from the underside of the cap portion, is in fluid communication with the canister and retains a float therein. The float is slidingly retained in the float retaining tube for sealingly engaging a lower end of the water feed tube, so that the engagement of the float with the feed tube, both the float and the feed tube being retained within the float retaining tube, controls the flow of water into the housing. The cap portion, the water feed tube, the float, and the float retaining tube are secured as a unit into the humidifier housing.

As water evaporates into the respiratory gases, the water level will fall, lowering the float and opening the water feed tube to replenish the canister. If desired, a sleeve of water absorbing, paper-like material is placed within the canister to act as a wick for the promotion of evaporation within the humidifier chamber.

In another embodiment, the cap portion of the invention, including the gas inlet port, gas delivery port, water delivery port, as well as the depending water feed tube, float assembly, and float retaining tube, may be provided as an interchangeable unit for use with currently available evaporative heater units. The above-described assembly may be provided in a humidification chamber which is defined by a cap portion and a plastic housing with a heat conductive base plate. Water and air are introduced into the humidification chamber as before, and the base plate conducts heat into the humidification chamber. If desired, the humidification chamber housing may be fabricated in various volumetric configurations to adapt to various heater units, and also to be more compatible with a certain patient group, such as adults or children.

In addition, a supplemental, vertically projecting coil of heat conductive material, such as aluminum, may be placed upon the base plate and engaged at its upper end with the underside of the cap portion. The coil enhances the conduction of heat into the humidification chamber. As in the previous embodiment, a sleeve of wicking material may be placed in the humidification chamber to promote evaporation.

BRIEF DESCRIPTION OF THE DRAWINGS

FIG. 1 is a fragmentary front elevational view of the heated cartridge humidifier of the invention shown positioned within a heater unit shown in section;

FIG. 2 is a plan elevational view of the cap portion of the heated cartridge humidifier of FIG. 1;

FIG. 3 is an underside elevational view of the cap portion of FIG. 2;

FIG. 5 is a front elevational view, in partial section, of an alternate embodiment of the cartridge humidifier of FIG. 1;

FIG. 6 is a front elevational view, in partial section, of an alternate configuration for the humidification chamber of the embodiment of FIG. 5;

DETAILED DESCRIPTION OF THE PREFERRED EMBODIMENT

Figure 4:
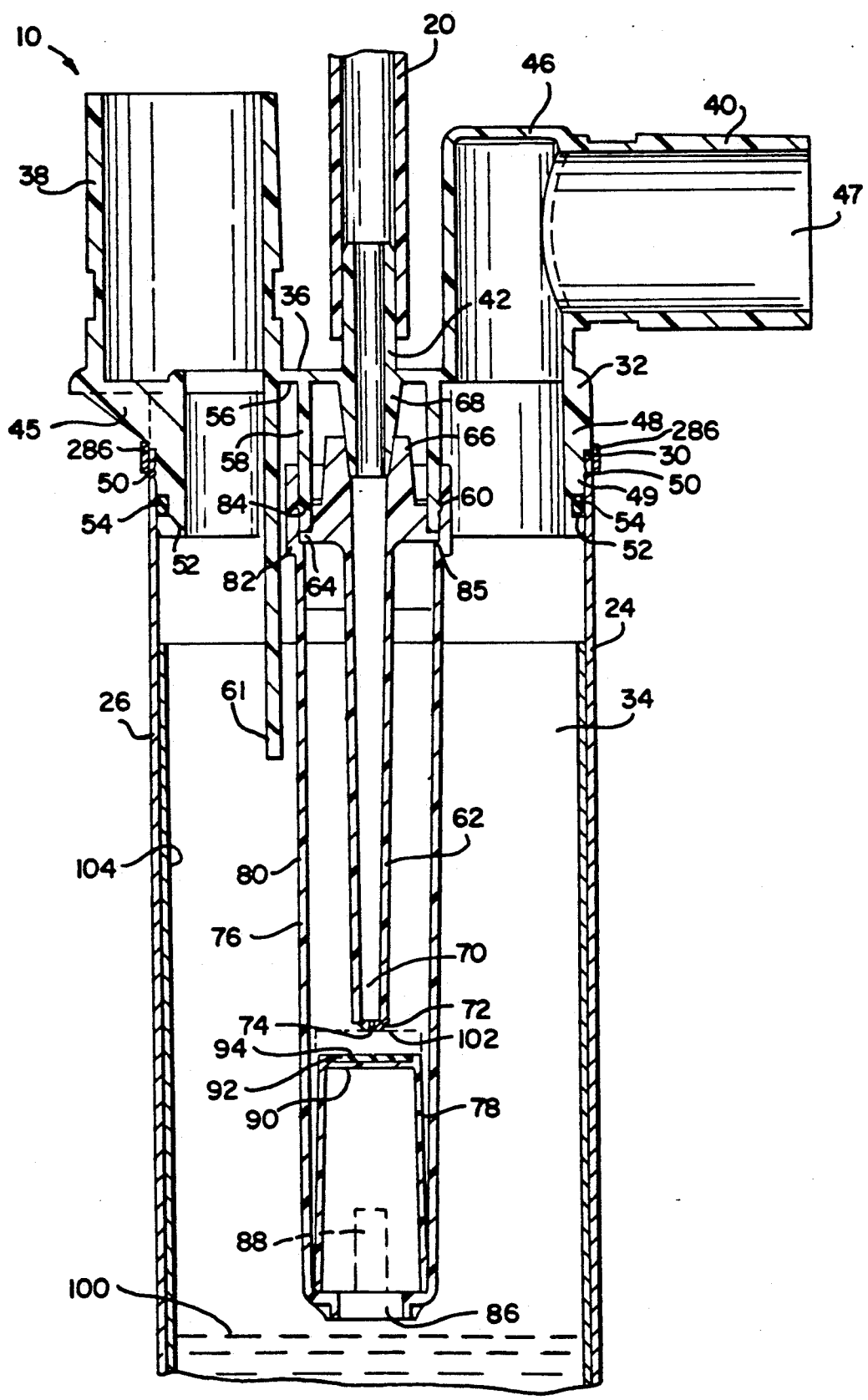
FIG. 4 is a fragmentary vertical sectional view of the heated cartridge humidifier of FIG. 1.

Referring now to FIG. 1, the heated disposable cartridge humidifier of the invention is generally designated 10. The cartridge 10 is shown being supplied sterile water 12 from a gravity feed, collapsible water supply bag 14. The bag 14 is suspended at a specified height by a rack 16 as is known in the medical field. At least one outlet 18 is located at a lower end of the bag 14. Unused outlets 18 remain sealed. A water delivery tube 20, preferably of the flexible, transparent plastic type, connects the bag 14 with the humidifier 10.

The humidifier 10 is configured to be operationally engaged with a conventional heating unit 22, such as a base unit or a supportable heater sleeve as is known in the art. The humidifier 10 includes a humidifier housing 24, also described as a canister, configured to operationally engage the heating unit 22 for receiving heat therefrom. In the preferred embodiment, the canister 24 is basically a cylindrical body 26 with an integral, sealed bottom 28, an open upper end 30 and is fabricated of cold drawn aluminum. However, it is contemplated that other types of conventionally available inexpensive heat conductive materials may be used to fabricate at least a portion of the canister 24.

A cap portion 32 is configured to sealingly engage the open upper end 30 of the canister 24 so as to define a humidifier chamber 34 (best seen in FIG. 4). The cap portion 32 has an upper surface 36 having a substantially cylindrical gas inlet portion 38, an elbow-shaped gas delivery port 40, and a nipple-like water delivery port 42 adapted to be connected to the water delivery tube 20. It should be noted that all of the ports 38, 40, and 42 are in fluid communication with the canister 24 as well as the chamber 34, and may be provided in different configurations depending on the application. However, the respective outer diameters of the gas inlet port 38 and the gas delivery port 40 are each preferably 22 mm.

Referring now to FIGS. 1–4, the ports 38 and 40 are arranged upon the cap portion 32 so as to maximize the available space while ensuring sufficient volumetric capacity for the respiratory gases passing therethrough. As such, the gas inlet port 38 is axially offset on the upper surface 36 so that an outer edge 44 of the cap portion 32 generally bisects the inlet port. The offset nature of the port 38 may require additional support members, such as the gusset 45. In addition, the gas delivery port 40 includes a vertically projecting portion 46 which has an irregular, triangle-like cross-section. This shape is designed to maximize the gas flow from the humidifier 10 while allowing sufficient room on the upper surface 36 for the ports 38, 40 and 42. A laterally projecting portion 47 is basically cylindrical.

The cap portion 32 also includes a depending annular skirt 48, an outer surface of which having at least one annular sealing groove 50, of which two are depicted. The skirt 48 also has a relatively larger O-ring groove 52 disposed below the grooves 50. The O-ring groove 52 contains an O-ring 54 disposed there to seal the cap portion 32 upon the canister 24.

An underside 56 of the cap portion 32 includes a centrally located depending cylindrical formation 58 which is coaxial with the water delivery port 42. The cylindrical formation 58 is provided with an annular locking rib 60 integrally formed thereon. In the preferred embodiment, the cap portion 32, including the ports 38, 40, 42 and the formation 58 is molded as a single piece from suitable plastic material such as polycarbonate or polypropylene. It is preferred that the underside 56 be provided with a depending wall or baffle portion 61 which further defines the gas inlet port 38 (best seen in FIG. 4). By extending the baffle 61 into the humidifier housing, the incoming air will be deflected laterally across the surface of the water, i.e., in a portion of the housing having a higher humidity, thus accelerating the humidification of the incoming air. Thus, the preferred length of the baffle 61 is approximately ⅛ inch or a distance providing sufficient air deflection without immersing the baffle in the water of the housing.

Referring now to FIG. 4, a water feed tube 62 is configured to depend from the underside 56 of the cap portion 32. More specifically, the feed tube 62 has a radially projecting flange 64 which is held in abutting relationship against a lower edge of the cylindrical formation 58. The feed tube 62 also has an inlet formation 66 which is dimensioned to matingly engage a lower end 68 of the water delivery port 42. A lower end 70 of the feed tube 62 has a depending nipple formation 72 with an axially disposed opening 74. The feed tube 62 is provided in a length dimensioned such that the lower end 70 will approximate the desired water level in the humidifier chamber 34. In the preferred embodiment, the feed tube 62 is molded of polypropylene, although other materials may be equally suitable.

A float retaining tube 76 is provided to secure the water feed tube 62 to the underside 56 of the cap portion 32. Another function of the retaining tube 76 is to retain a float 78 is operational proximity to the lower end 70 of the water feed tube 62. To this end, the retaining tube 76 includes an elongate body 80 having a collar 82 located at an upper end thereof. The body 80 and the collar 82 are dimensioned to circumscribe the water feed tube 62.

The collar 82 has an annular groove 84 dimensioned to lockingly engage the annular locking rib 60 on the depending cylindrical formation 58. In addition, the collar 82 includes a shoulder 85 which engages the radially projecting flange 64 in order to securely retain the water feed tube 62 against the depending cylindrical formation 58.

The float retaining tube 76 also includes a lower opening 86, as well as at least one "window" opening 88 (shown hidden) so that the tube is in fluid communication with the humidifier chamber 34, as well as the canister 24. In the preferred embodiment, the retaining tube 76 is also molded of polypropylene, although the use of other equivalent materials is contemplated.

The float 78 is basically a tube of buoyant material, such as polyethylene, and has a closed-off, watertight upper end 90. The float 78 is dimensioned to be slidingly retained in a lower end of the float retaining tube 76. The end 90 is formed so as to have a recess 92 into which a disk or pad 94 of rubber or other resilient material may be secured. The dimensions and material used for the pad 94 are such that upon contact with the nipple formation 72, the axial opening 74 will be sealed, effectively cutting off the flow of water 12 into the canister 24.

A sleeve 104 of water-absorbent wicking material may be placed into the canister 24 and positioned against the interior surface thereof. The sleeve 104 is preferably made of paper or a paper-like material which draws water upwardly from the bottom of the canister 24 and into the humidifier chamber 34 to enhance evaporation, and to facilitate the creation of heated water vapor for transmittal to the patient.

Referring now to FIGS. 5-7 and 8, an alternate embodiment of the cartridge humidifier 10 is depicted and is generally designated 110. The humidifier 110 is basically designed to be used with heating units of the type designated 122 (best seen in FIG. 8) which cannot accept the humidifier housing or canister 24 of the humidifier 10.

The humidifier 110 includes a cap portion 132 which is for the most part identical to the cap portion 32, and includes an upper surface 136 having a substantially cylindrical gas inlet port 138, an elbow-shaped gas delivery port 140, and a nipple-like water delivery port 142 adapted to be connected to the water delivery tube 20 (best seen in FIG. 1). In addition, the humidifier 110 includes a float retaining tube 176 enclosing a water feed tube 162 and a float 178 in operational proximity to the lower end 170 of the water feed tube in the same arrangement as the float retaining tube 76, the water feed tube 62, and the float 78 described in relation to FIGS. 1-4. If desired, a baffle 61 may also be included.

Specifically, it is preferred that the float retaining tube 176 frictionally engages a depending formation (not shown) of the cap portion 132 to retain both the water feed tube 162 and the float 178 in operational relationship against the underside of the cap portion 132. In fact, in the preferred embodiment, the cap portion 32, the water feed tube 62, the float retaining tube 76 and the float 78 may be withdrawn from the canister 24 and substituted as a unit into the humidifier 110.

Referring now to FIG. 5, the most significant difference between the humidifier 10 and the humidifier 110 is that the canister 24 has been replaced by a humidification chamber generally designated 200. The humidification chamber 200 is defined by a housing 202, preferably fabricated of a self-supporting, transparent plastic material such as polypropylene, a base plate 204, preferably made of a heat conductive material, such as metal, and the cap portion 132. Aluminum is the the preferred material for the base plate 204, although other lightweight, inexpensive metals are contemplated.

The housing 202 defines an open upper end 206 which is dimensioned to frictionally accommodate the narrowed lower portion 49 of the skirt 48 (best seen in FIG. 4) of the humidifier 10, as well as the corresponding elements 148, 149 of the humidifier 110. The housing 202 also includes an upper portion 208, also referred to as the vaporization chamber, and a lower portion 210 which contains the water reservoir. The upper portion 208 and the lower portion 210 are in complete fluid communication with each other. Also, as is the case with the humidifier 10, water enters the housing 202 through an opening 186 in the bottom of the float retaining tube 176.

In the embodiment of FIG. 5, which is preferred for use in pediatric respiratory therapy, the lower portion 210 is of a relatively larger diameter that the upper portion 208, and is integrally joined thereto by a shoulder 212. It is believed that the relatively narrower vaporization chamber represented by the upper portion 208 will prevent pediatric patients from becoming hyperventilated. The volume of the housing 202 is approximately 380 ml.

A lower end 214 of the housing 202 has a radially projecting flange 216 which forms the attachment point for the base plate 204. Basically a flat, circular plate of heat conductive material such as metal, with a preferred material being aluminum, the base plate 204 includes an annular, generally wedge-shaped band 218. The band 218 is positioned on the base plate 204 to maintain the centralized disposition of the housing 202 upon the plate. In addition, the base plate 204 is provided with a peripheral lip 220, which is bent vertically upward, as shown on the right side of FIG. 5, and then bent backward or crimped over the flange 216 of the housing 202 as depicted on the left side of FIG. 5. The base plate 204 and the housing 202 are secured to each other through the above-described bending and crimping of the lip 220 over the flange 216, and through the alignment function of the annular band 218.

While the housing 202 is preferred for use in pediatric respiratory therapy, in many cases, and for treatment of adult patients, a larger capacity vaporization chamber is preferred. Referring now to FIG. 6, another embodiment of the humidifier 110 is shown and is generally designated 110a. Components of the humidifier 110a which are identical to those of the humidifier 10 have been designated with identical reference numerals.

When treatment for adult patients is called for, the humidification chamber 200a is manufactured with a larger volume housing, designated generally at 222. The housing 222 is preferably made of the same material as the housing 202, and has an open upper end 224 which is virtually identical in dimension to the upper end 206 of the housing 202. In this way, the housing 222 will easily accommodate the cap portion and float assembly described previously. These structural changes in the housing 222 create an approximate volume of 592 ml.

A shoulder 226 defining an upper portion 228 from a lower portion 230 is located significantly closer to the upper end 224 than is the shoulder 212 in the housing 202. A lower end 232 of the housing 222 is provided with a radially projecting flange 234 which is virtually identical in dimension to the flange 216 of the housing 202, so that both housings may be used with the same base plate 204. The base plate 204 is preferably affixed to the flange 234 by means of the lip 220 in the same manner as described in relation to FIG. 5.

Figure 7:
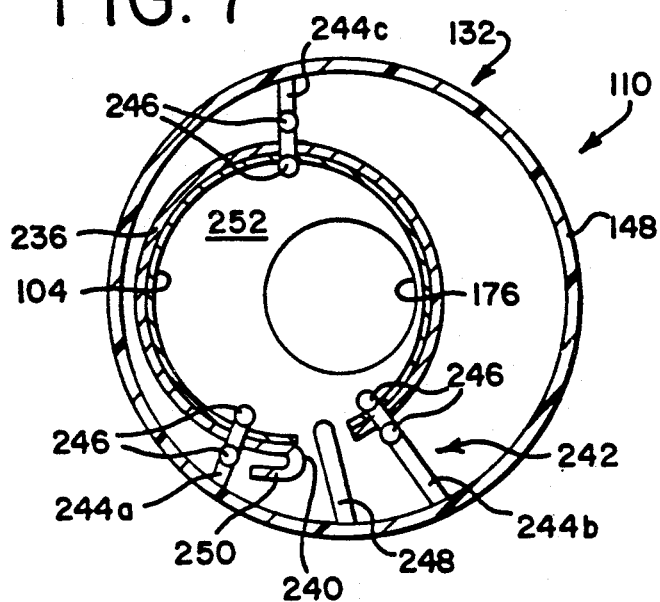
FIG. 7 is a sectional view taken along the line 7—7 of FIG. 5 and in the direction indicated generally.

Referring now to FIGS. 5-7, in some applications it has been found that increased vaporization may be induced within the humidification chamber 200 through the use of a metallic coil 236, having a lower end 238 in contact with the base plate 204, and projecting vertically into the corresponding upper portions 208, 228 of the housings 202, 222. The coil 236 is preferably made of a flat piece of aluminum which is worked into a generally cylindrical shape, being open along a vertical line at one peripheral point to define a narrowed vertical slot 240 (best seen in FIG. 7).

The coil 236 is retained within the housing 202, 222 by a lug system 242 which is molded into the underside of the cap portion 132 (best seen in FIG. 7). The lug system 242 preferably includes at least one and preferably three inwardly projecting arms 244a, 244b and 244c, each having a pair of spaced, depending retaining lugs 246. The retaining lugs 246 are disposed to straddle the upper edge of the coil 236 to maintain its position within the housing 202, 222. The position of the float retaining tube 176, as well as the water feed tube 162, and the float 178 is indicated diagrammatically by a circle bearing the reference numeral 176. It will be evident that the coil 236 substantially circumscribes the float retaining tube 176.

A positioning arm 248 projects inwardly from the cap portion 132 to engage the vertical slot 240. In this way, the position of the slot 240 relative to the cap portion 132 is maintained and rotation of the coil about a vertical axis is prevented. The fabrication of the coil 236 may include the formation of a double-over edge portion 250 which defines one side of the slot 240.

The preferred positioning of the coil 236 within the housing 202, 222 is such that, due to its almost cylindrical configuration, and its contact with the base plate 204, which is in contact with a heated surface, a zone of relatively higher temperature is created within the coil 236. This area, generally designated 252, will thus promote vaporization, and as such, is preferably positioned within the housing 202, 222 to receive the incoming air from the gas inlet port 138. Vaporization is further facilitated through the use of a sleeve 104 of wicking material placed within the area 252 and against the coil 236. Heated, vaporized air is allowed to escape the area 252 through the slot 240, and circulates within the chamber defined by the housing 202, 222 until it is drawn up the gas delivery port 140 for delivery to the patient.

Figure 8:
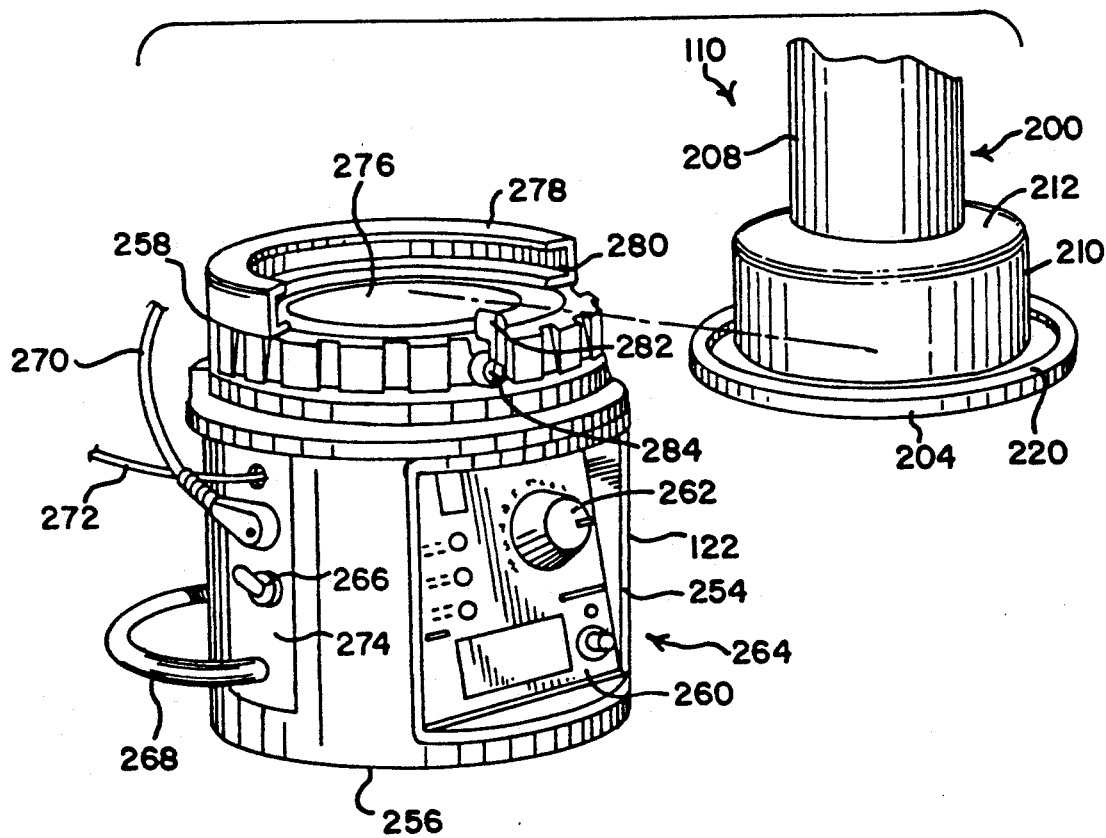
FIG. 8 is a front perspective exploded view of a conventionally available heating unit with a fragmentary view of the cartridge humidifier of FIG. 5 being installed therein.

Referring now to FIG. 8, the heating unit 122 is designed to provide heat to the water contained in the humidification chamber 200, 200a so that the water is more easily vaporized, and is provided to the patient at a temperature which is as comfortable as possible. Included in the heating unit 122 is a housing 254 having a lower end 256 designed for positioning upon a horizontal surface such as a shelf or table, and an upper end 258.

The housing 254 has a control panel 260 equipped with a temperature setting control 262, and various temperature warning lights and alarm indicators, generally designated 264. A power switch 266, a power cord 268, and temperature sensor inputs 270, 272 may be located on a panel 274 on the housing 254. The upper end 258 of the housing 254 has a heating surface 276 which is partially surrounded by a generally semicircular bracket 278. The bracket 278 is "C" or channel-shaped in cross-section to define an inwardly opening channel 280. A pivoting locking tab 282 is mounted to the upper end 258 of the housing 254 through the use of a pivot member 284, which may be a pin or a threaded fastener.

The dimensions of the folded over and crimped peripheral lip 220 of the base plate 204 and the flanges 216, 234 are such that the humidifier 110, 110a may be slid into the channel 280 to engage the bracket 278. The locking tab 282 is then moved to the vertical position indicated in FIG. 8 to maintain the humidifier 110, 110a in desired operational alignment upon the heating plate 276. In this position, the metallic or otherwise conductive base plate 204 will be heated by the heating plate 276.

In operation, and referring now to FIGS. 1 and 4, the humidifier 10, as well as the humidifiers 110 and 110a, are assembled by placing the float 78, 178 into the lower end of the float retaining tube 76, 176 and positioning the water feed tube 62, 162 in the retaining tube 76, 176 so that the flange 64 engages the shoulder 85. The collar 82 is then pushed onto the depending cylindrical formation 58 until the rib 60 lockingly engages the groove 84. At this time during the assembly of the humidifier 10, if desired, the sleeve 104 of water-absorbent, wicking material is placed into the canister 24 and positioned against the interior surface thereof. In the case of the humidifiers 110, 110a, the coil 236 is positioned between the cap portion 132 and the base plate 204, and the sleeve 104 of wicking material may be placed against the inner surface of the coil.

Referring now to the humidifier 10, the cap portion 32 is then placed over the open end 30 of the canister 24 and sufficient pressure is applied to secure the cap portion therein. In applications where the sealing capabilities of the sealing grooves 50 and the O-ring 54 may need to be supplemented, a strip of adhesive tape 286 (best seen in FIG. 4) may be employed, which is placed around the seam formed by the junction of the cap portion 32 and the upper edge of the canister 24. Next, the canister 24 is placed in the heating unit 22, and gas input and delivery hoses 96, 98 respectively, are connected to the corresponding ports 38 and 40 (best seen in FIG. 1).

Referring now to the humidifier 110, 110a, the cap portion 132 is assembled in the identical manner as the cap portion 32. Once the coil 236 is properly positioned by the lug system 242, and the wicking sleeve 104 is installed, the cap portion 132 may be secured upon either the juvenile housing 202, or the adult housing 222. An O-ring 288 secured within an annular groove 290 may be used to sealingly secure the cap portion 132 to the housing 202 or 222. If desired, adhesive tape 286 (best seen in FIG. 4) may also be used.

An alternative configuration which may be used to seal the cap portion 132 to the housing 202, 222, and which may also be used on the humidifier 10 is depicted in FIG. 6. In this embodiment, the upper portion 228 of the housing 222 is provided with a bayonet groove 292, and the lower portion 149 of the skirt 148 has an outwardly projecting bayonet lug 294. Thus, the cap portion 132 may be sealingly engaged upon the housing 222 by a push-and-twist operation. It is also contemplated that the lug 294 may be located on the housing 222, and the groove 292 may be located on the skirt 148. Once assembled, the humidifier 110, 110a may be installed upon the heater unit 112 by being slid into the channel 280 and locked into position by the locking tab 282.

In both humidifiers 10, 110, once the water delivery tube 20 is connected to the water delivery port 42, sterile water 12 will pass through the water feed tube 62, 162 out the opening 86, 186 and the windows 88, and into the canister 24 or the housing 202, 222. As the water level 100 (best seen in FIG. 4) rises, the float 78, 178 will rise in the retaining tube 76, 176 until the pad 94 contacts and sealingly engages the axial opening 74 in the nipple formation 72.

Upon sealing contact between the pad 94 and the opening 74, shown at the point 102 (best seen in FIG. 4), the flow of water 12 into the canister 24 or the housing 202, 222 will cease. As respiratory gases flow through the heated and humidified humidifier chamber 34, the water level 100 will fall due to evaporation. The evaporation may be enhanced by the insertion of the sleeve 104 of wicking material. When the water level 100 falls, the float 78 will also fall, allowing the lost water to be replaced. As water 12 is used by the humidifier, the water bag 14 will gradually collapse as it empties. In this manner, the problems of venting and bacterial infection experience with conventional heated humidifiers are avoided. In addition, the present invention provides a simple, easily assembled, and effective humidifier unit.

While a particular embodiment of the heated cartridge humidifier of the invention has been shown and described, it will be appreciated by those skilled in the art that changes and modifications may be made thereto without departing from the invention in its broader aspects and as set forth in the following claims.

What is claimed is:

1. A heated cartridge humidifier for use with a collapsible gravity feed water supply container and a separate heating means, and, when engaged in the heating means, said humidifier being adapted for heating and humidifying a breathable gas to be inhaled by a patient, said humidifier comprising:
   a humidifier housing configured to operationally engaged the heating means for receiving heat therefrom, said housing having an open upper end;
   a cap portion configured to sealingly engage said open upper end of said humidifier housing, said cap portion having a gas inlet port, a gas delivery port, and a water delivery port adapted to receive water from the container, all of said ports being in fluid communication with said humidifier housing;
   a water feed tube depending from an underside of said cap portion;
   float retaining means circumscribing said feed tube, depending from said underside of said cap portion, being in fluid communication with said humidifier housing and dimensioned to retain a float therein, said float retaining means including a float retaining tube with an upper end configured for secure engagement with a formation depending from said underside of said cap portion;
   a float dimensioned to be slidingly retained in said float retaining tube and having an upper end for sealingly engaging a lower end of said water feed tube, so that the engagement of said float with said feed tube, both said float and said feed tube being retained within said float retaining tube, controls the flow of water into said humidifier housing; and
   said cap portion, said water feed tube, said float, and said float retaining tube being secured as a unit into said humidifier housing.

2. The cartridge humidifier as defined in claim 1 wherein said humidifier housing is fabricated of a plastic material and includes a metallic base plate.

3. The cartridge humidifier as defined in claim 1 wherein said humidifier housing has a volumetric capacity of approximately 380 ml.

4. The cartridge humidifier as defined in claim 1 wherein said humidifier housing has a volumetric capacity of approximately 592 ml.

5. The cartridge humidifier as defined in claim 1 wherein said humidifier housing includes a heat conductive coil disposed within said housing to substantially circumscribe said float retaining means.

6. The cartridge humidifier as defined in claim 5 wherein said coil is substantially cylindrical in shape and defines a vertical slot.

7. The cartridge humidifier as defined in claim 5 wherein said cap portion includes means located on an underside thereof for retaining the position of said coil.

8. The cartridge humidifier as defined in claim 7 wherein said means for retaining the position of said coil includes at least one inwardly projecting lug arm having at least one depending positioning lug.

9. The cartridge humidifier as defined in claim 8 wherein said means for retaining further includes at least one inwardly projecting positioning arm.

10. The cartridge humidifier as defined in claim 1 further including wicking means for enhancing evaporation occurring within said humidifier housing.

11. The cartridge humidifier as defined in claim 5 further including a sleeve of wicking material disposed within said coil.

12. The cartridge humidifier as defined in claim 1 wherein said cap portion has an annular recess configured to accommodate a resilient sealing ring therein, and said cap portion is sealed to said humidifier housing with adhesive tape.

13. The cartridge humidifier as defined in claim 1 wherein said cap portion is sealingly secured to said humidifier housing by a bayonet lug and groove structure.

14. The cartridge humidifier as defined in claim 2 wherein said housing is fabricated of deep drawn aluminum.

15. The cartridge humidifier as defined in claim 1 wherein said gas inlet port, said gas delivery port, and said water inlet port are integrally formed on said cap portion.

16. The cartridge humidifier as defined in claim 15 wherein said gas inlet port is cylindrical and is axially offset upon said cap portion.

17. The cartridge humidifier as defined in claim 16 wherein said cap portion has an annular recess configured to accommodate a resilient sealing ring therein.

18. The cartridge humidifier as defined in claim 1 wherein said water feed tube is retained against an underside of said cap portion by said float retaining means.

19. The cartridge humidifier as defined in claim 1 wherein said cap portion has a depending cylindrical formation with a central bore in communication with said water inlet port, and a locking formation for engaging said float retaining means.

20. The cartridge humidifier as defined in claim 19 wherein said feed tube is retained against said cylindrical formation by said float retaining means.

21. The cartridge humidifier as defined in claim 20 wherein said feed tube has an upper end with a radially projecting flange configured to be retained against a lower edge of said cylindrical formation.

22. The cartridge humidifier as defined in claim 1 wherein said float retaining tube has an upper end having an annular collar defining a shoulder, and a lower end with at least one opening for fluid communication with said housing.

23. The cartridge humidifier as defined in claim 19 wherein said float retaining means has an annular collar at an upper end thereof and an annular groove in said collar configured to lockingly engage said locking formation on said depending cylindrical formation.

24. The cartridge humidifier as defined in claim 1 wherein said float includes a tubular body with an upper end having a pad of resilient material affixed thereto so as to sealingly engage a lower end of said water feed tube.

25. The cartridge humidifier as defined in claim 1 wherein said gas inlet port includes a baffle formation which depends into said humidifier housing.

26. A disposable heated cartridge humidifier for use with a collapsible, gravity feed, water supply container and a separate heating means, and, when engaged in the heating means, said humidifier being adapted for heating and humidifying a breathable gas to be inhaled by a patient, said humidifier comprising:
a humidifier housing configured to operationally engage the heating means for receiving heat therefrom, said humidifier housing having an open end and a lower end having a heat conductive surface for receiving heat from the heating means;
a cap portion configured to sealingly engage said open upper end of said humidifier housing, said cap portion having a gas inlet port, a gas delivery port, and a water delivery port adapted to receive water from the container, all of said ports being in fluid communication with said humidifier housing;
a water feed tube depending from an underside of said cap portion;
float retaining means circumscribing said feed tube, depending from said underside of said cap portion, being in fluid communication with said humidifier housing and dimensioned to retain a float therein;
a float dimensioned to be slidingly retained in said float retaining tube and having an upper end for sealingly engaging a lower end of said water feed tube, so that the engagement of said float with said feed tube, both said float and said feed tube being retained within said float retaining tube, controls the flow of water into said humidifier housing;
said cap portion, said water feed tube, said float, and said float retaining tube being secured as a unit into said humidifier housing; and
said humidifier housing including a heat conductive coil disposed within said housing to substantially circumscribe said float retaining means.

27. The cartridge humidifier as defined in claim 26 wherein said coil is substantially cylindrical in shape and defines a vertical slot.

28. The cartridge humidifier as defined in claim 26 wherein said cap portion includes means located on an underside thereof for retaining the position of said coil.

29. The cartridge humidifier as defined in claim 26 wherein said means for retaining the position of said coil includes at least one inwardly projecting lug arm having at least one depending positioning lug.

30. The cartridge humidifier as defined in claim 26 wherein said coil is positioned within said humidifier housing to be in communication with said gas inlet port.

31. A disposable, unitized, heated cartridge humidifier device, for use with a separate heating means, when engaged in the heating means, said humidifier adapted for heating and humidifying a breathable gas to be inhaled by a patient and comprising:
a collapsible water supply gravity feed bag having a water delivery tube depending therefrom;
a canister configured to operationally engage the heating means for receiving heat therefrom, said canister having an open upper end;
a cap portion configured to sealingly engage said open upper end of said canister to define a humidifier chamber for humidifying the breathable gas as it is passed therethrough, said cap portion having a gas inlet port, a gas delivery port, and a water delivery port adapted to be connected to said water delivery tube to receive water from said bag, all of said ports being in fluid communication with said canister;
a water feed tube depending from an underside of said cap portion;
float retaining means circumscribing said feed tube, depending from said underside of said cap portion, being in fluid communication with said canister and dimensioned to retain a float therein, said float retaining means including a float retaining tube with an upper end configured for secure engagement with a formation depending from said underside of said cap portion;
a float dimensioned to be slidingly retained in said float retaining tube and having an upper end for sealingly engaging a lower end of said water feed tube, so that the engagement of said float with said feed tube, both said float and said feed tube being retained within said float retaining tube, controls the flow of water through said float retaining tube and into said canister;
said cap portion, said water feed tube, said float, and said float retaining tube being secured as a unit into said canister; and
following use, said unitized humidifier being disengageable from the heating means for disposal and for maintaining sterile conditions.

* * * * *